United States Patent
Gallou et al.

(10) Patent No.: US 10,723,735 B2
(45) Date of Patent: Jul. 28, 2020

(54) PROCESS FOR PREPARING 1-(4-METHANESULFONYL-2-TRIFLUOROMETHYL-BENZYL)-2-METHYL-1H-PYRROLO [2,3-B]PYRIDIN-3-YL-ACETIC ACID

(71) Applicant: Novartis AG, Basel (CH)

(72) Inventors: Fabrice Gallou, Basel (CH); Philipp Lustenberger, Basel (CH); Christian Mathes, Basel (CH); Qiangbiao Pan, Taizhou, Zhejiang (CN); Benli Zou, Taizhou, Zhejiang (CN)

(*) Notice: Subject to any disclaimer, the term of this patent is extended or adjusted under 35 U.S.C. 154(b) by 0 days.

(21) Appl. No.: 16/495,275

(22) PCT Filed: Mar. 29, 2018

(86) PCT No.: PCT/IB2018/052188
§ 371 (c)(1),
(2) Date: Sep. 18, 2019

(87) PCT Pub. No.: WO2018/178926
PCT Pub. Date: Oct. 4, 2018

(65) Prior Publication Data
US 2020/0031824 A1    Jan. 30, 2020

(30) Foreign Application Priority Data

Apr. 1, 2017 (CN) .................. PCT/CN2017/079244

(51) Int. Cl.
*C07D 471/04* (2006.01)
*B01J 23/44* (2006.01)
*B01J 27/128* (2006.01)

(52) U.S. Cl.
CPC ............ *C07D 471/04* (2013.01); *B01J 23/44* (2013.01); *B01J 27/128* (2013.01)

(58) Field of Classification Search
CPC ..................................................... C07D 471/04
USPC ......................................................... 546/113
See application file for complete search history.

(56) References Cited

FOREIGN PATENT DOCUMENTS

| WO | 2005/123731 | 12/2005 | |
|---|---|---|---|
| WO | 2007/068418 | 6/2007 | |
| WO | WO 2017/056001 A1 * | 9/2017 | ........... C07D 471/04 |

OTHER PUBLICATIONS

Sandham et al.: "Discovery of Fevipiprant (NVP-QAW039), a potent and selective DP2 receptor antagonist for treatment of asthma", ACS Medical Chemistry Letters, vol. 8, pp. 582-586, Apr. 25, 2017.

* cited by examiner

*Primary Examiner* — Charanjit Aulakh
(74) *Attorney, Agent, or Firm* — Daniel Woods

(57) ABSTRACT

This invention relates to novel processes for synthesizing [1-(4-Methanesulfonyl-2-trifluoromethyl-benzyl)-2-methyl-1H-pyrrolo[2,3-b]pyridin-3-yl]-acetic acid and to intermediates that are used in such processes.

18 Claims, 1 Drawing Sheet

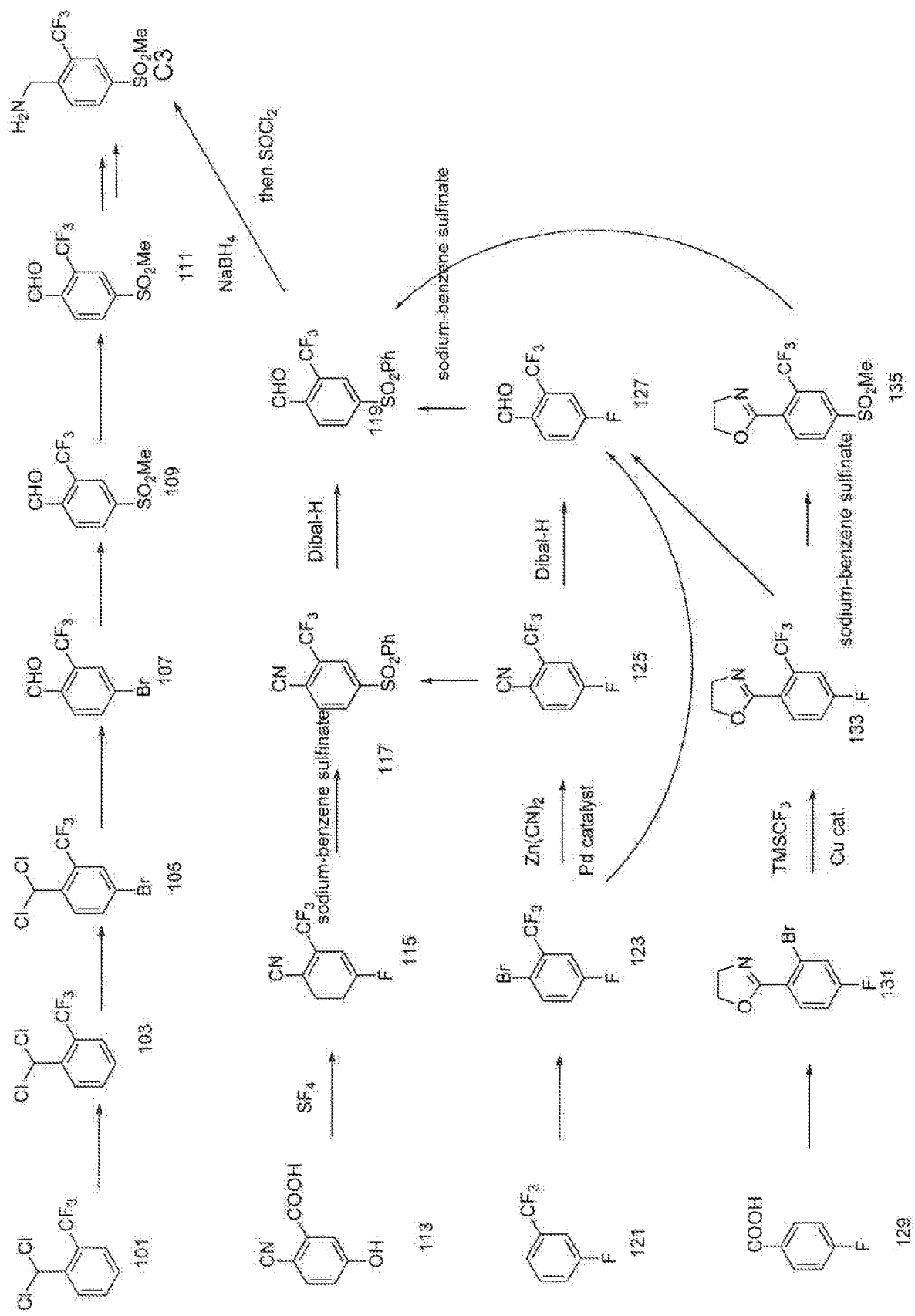

PROCESS FOR PREPARING 1-(4-METHANESULFONYL-2-TRIFLUOROMETHYL-BENZYL)-2-METHYL-1H-PYRROLO [2,3-B]PYRIDIN-3-YL-ACETIC ACID

TECHNICAL FIELD

This invention relates to novel processes for synthesizing 1-(4-Methanesulfonyl-2-trifluoromethyl-benzyl)-2-methyl-1H-pyrrolo[2,3-b]pyridin-3-yl-acetic acid utilizing a 7-aza-indo-3-yl acetic acid derivative intermediate.

BACKGROUND OF THE DISCLOSURE

The pharmaceutically active compound 1-(4-Methanesulfonyl-2-trifluoromethyl-benzyl)-2-methyl-1H-pyrrolo[2,3-b]pyridin-3-yl-acetic acid ("Compound A") is an antagonist of the G-protein coupled chemokine receptor homologous molecule expressed on Th2 lymphocytes ("CRTh2") that is useful for the treatment of several disorders such as asthma and atopic dermatitis. Compound A has the following chemical structure:

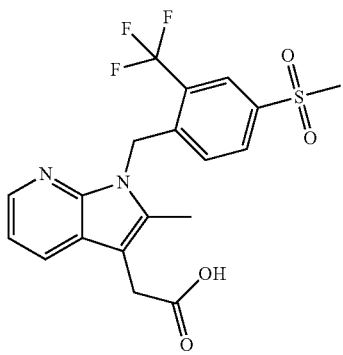

Compound A

[1-(4-Methanesulfonyl-2-trifluoromethyl-benzyl)-2-methyl-1H-pyrrolo[2,3-b]pyridin-3-yl]-acetic acid Compound A, methods of synthesizing Compound A and methods of treating various disorders using Compound A are referred to in U.S. Pat. No. 7,666,878 which issued on May 10, 2011, the contents of which are herein incorporated by reference in its entirety.

Although methods of producing Compound A are known, as set forth, for example, in PCT/IB2016/05577, and the above referenced patent, the present invention discloses for the first time a method of producing Compound A which has fewer steps, has a higher yield, and has a higher selectivity for Compound A. The invention accomplishes these features primarily via the use of an aza-indo-3-yl acetic acid derivative intermediate which is described in more detail below. The advantages described above are exemplified in the examples that follow.

BRIEF SUMMARY OF THE DISCLOSURE

The invention relates to the compound 1-(2-(trifluoromethyl)-4-(methylsulfonyl)benzyl)-2-methyl-1H-pyrrolo[2,3-b]pyridine having the formula:

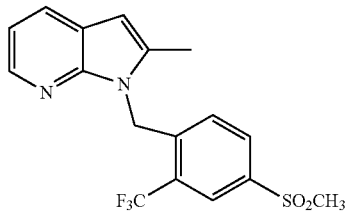

(C9)

This compound is useful as an intermediate in the synthesis of Compound A.

This invention also relates to a multi-step process for preparing C9. The process comprises first converting a compound of the formula:

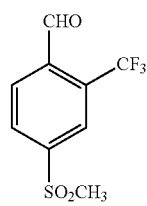

(C1)

4-(methylsulfonyl)-2-(trifluoromethyl)benzaldehyde to a compound of the following formula:

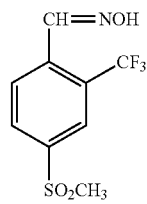

(C2)

4-(methylsulfonyl)-2-(trifluoromethyl)benzaldehyde oxime by adding hydroxylamine hydrochloride in the presence of one or more solvents such as water, ethanol (EtOH), dimethyl sulfoxide (DMSO) or other known solvents. Furthermore, the reaction is under basic conditions by adding a strong Lewis base such as sodium hydroxide. Compound C2 is then converted to a compound of the following formula:

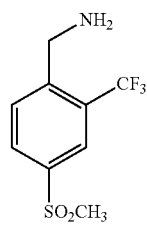

(C3)

(4-(methylsulfonyl)-2-(trifluoromethyl)phenyl)methanamine in the presence of ethyl acetate (EA) and a catalyst such as palladium on charcoal. C3 is reacted with a compound of the following formula:

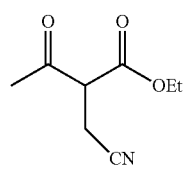
(C5)

ethyl 2-(cyanomethyl)-3-oxobutanoate
in the presence of an organic solvent such as ethanol and poly-phosphoric acid (PPA) to form the following compound:

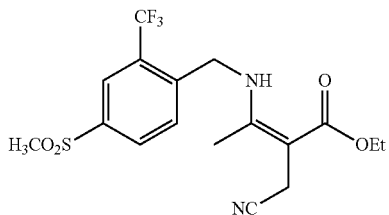
(C6)

Compound C5 is formed by reacting a compound of the formula:

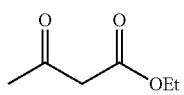
(C4)

ethyl 3-oxobutanoate
with a compound of the formula:

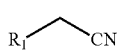

wherein R1 is a halogen selected from the group consisting of chloro, bromo or iodo in the presence of one or more solvents such as water, dichloro methane, EtONa and the like. If R1 is MsO or TsO, it may be used. Other alcoholate bases, compatible with the ester, such as NaOH, t-BuOK, t-BuONa KOH, and K2CO3, can be used in this step as well. In another embodiment, other reagents and solvents such as benzene, toluene, xylenes, cymene, organic and mineral acids can be used. Also as known in the art, various portic, mineral, organic or Lewis acids can be used in this step, as can various tetraalkoxypropanes.

Compound C6 is then converted to a compound of the following formula:

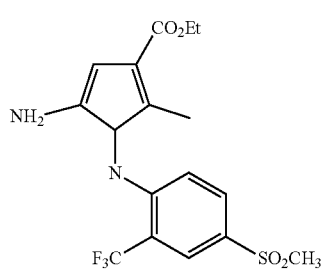
(C7)

ethyl 5-amino-2-methyl-1-(4-(methylsulfonyl)-2-(trifluoromethyl)benzyl)-1H-pyrrole-3-carboxylate
by adding EtONa in the presence of an organic solvent such as ethanol.

Compound C7 is then converted to a compound of the following formula:

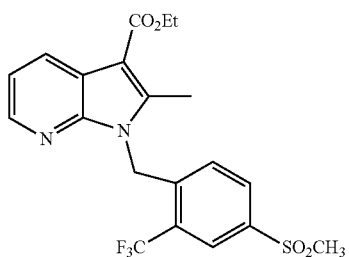
(C8)

ethyl 2-methyl-1-(4-(methylsulfonyl)-2-(trifluoromethyl)benzyl)-1H-pyrrolo[2,3-b]pyridine-3-carboxylate
by reacting it with 1,1,3,3-Tetramethoxypropane in the presence of a strong acid such as hydrochloric acid and a solvent such as ethanol. In other embodiments, other strong Lewis acids and other organic solvents can be used as is known in the art.

Finally, C8 is converted to C9 by reacting C8 with acetic acid (HOAc) in the presence of a strong acid such as hydrochloric acid. Alternatively, hydrolysis can be under basic conditions as known in the art.

The sequence of steps outlined above can be integrated into an overall scheme for the production of compound C9. Such an integrated process is generally comprised of the following steps under suitable reaction conditions described herein:
 (a) converting C1 to C2;
 (b) converting C2 to C3;
 (c) reacting compound C4 with halogenated acetonitrile to form C5;
 (d) reacting compound C3 with compound C5 to form C6;
 (e) converting compound C6 to C7;
 (f) converting compound C7 to C8; and
 (g) converting compound C8 to Compound 9.

Appropriate solvents useful in the above process include ethanol, toluene, isopropyl acetate, mixtures thereof or any appropriate solvent known in the art. Any one of these solvents, or combinations thereof, can be used in conjunction with any suitable catalyst as necessary. For example, palladium on charcoal can be used in conjunction with ethanol, toluene, isopropyl acetate, and mixtures thereof.

Furthermore, where necessary or convenient, various strong acids and bases can be substituted without deviating from the spirit of the invention. One of skill in the art will readily appreciate the use of varying Lewis acids and bases, as well as organic acids, bases and the like without departing from the spirit of the invention.

Advantageously, compound C9 can be converted to Compound A via one of several methods. In a preferred embodiment, compound C9 is reacted with Diazo-malonic acid dimethyl ester (DMDA) which has the following structure:

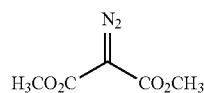

in the presence of a catalyst and an organic solvent to form the following compound:

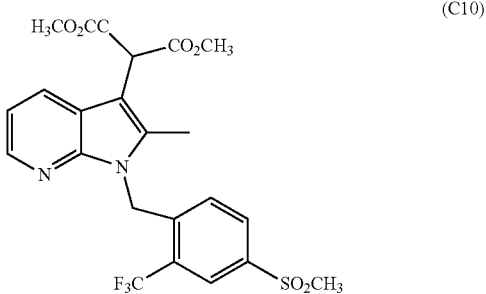

methyl 2-(2-methyl-1-(4-(methylsulfonyl)-2-(trifluoromethyl)benzyl)-1H-pyrrolo[2,3-b]pyridin-3-yl)-4-(methylperoxy)but-3-ynoate In a preferred embodiment the catalyst is cupric based, preferably Cu(acc)2. Other cupric sources such as CuSO4, Cu(acac)2, Cu(F6-acac)2, Cu(O2CCF3)2, Cu(acac)2 with ligands like triphenylphosphine (PPh3) or 2,2'-bipyridyl, 1,10-phenanthroline are utilized in other embodiments. In the preferred embodiment, the solvent is toluene, however other organic solvents such as DCM, benzene, xylene etc. can be used. C10 is then converted to Compound A by reacting sodium hydroxide in the presence of an alcohol such as ethanol. In other embodiments any other organic alcohol can be utilized.

In another embodiment, compound C9 is first reacted with a halogen in the presence of a solvent such as dimethyl formate (DMF) to form the following compound:

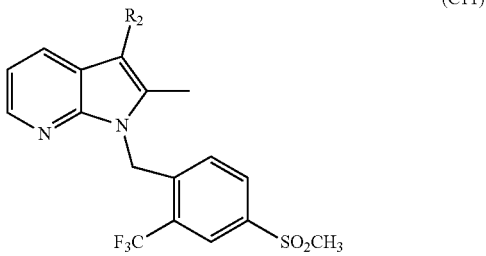

wherein $R_2$ is a halogenated compound selected from the group consisting of chloro, bromo, iodo, or fluoro. In a preferred embodiment $R_2$ is iodo. Compound C11 is then reacted with DMM in the presence of a polar aprotic solvent, a ligand and a catalyst to form C10. Preferred catalysts are copper based such as CuI, CuBr and CuCl. Suitable solvents include acetonitrile, N-butyl-pyrrolidine (NBP), tetrahydrofuran (THF), methyl tetrahydrofuran (MeTHF), water surfactants and combinations thereof. Suitable ligands include $K_2CO_3$.

C10 is then converted to Compound A by reacting sodium hydroxide in the presence of an alcohol such as ethanol.

BRIEF DESCRIPTION OF THE DRAWINGS

FIG. 1 is a reaction schematic showing several alternative methods for synthesizing compound C3.

DETAILED DESCRIPTION OF THE DISCLOSURE

In the discussion that follows, reference to compounds C1-C11 and Compound A are defined as they are defined above. The compounds and processes of this invention are depicted in the reaction scheme shown below with an overall aim of first forming intermediate C9. C9 can then be converted to compound A via one of several alternatives. The overall reaction scheme for the formation of C9 follows below:

Reaction Scheme for formation of C9

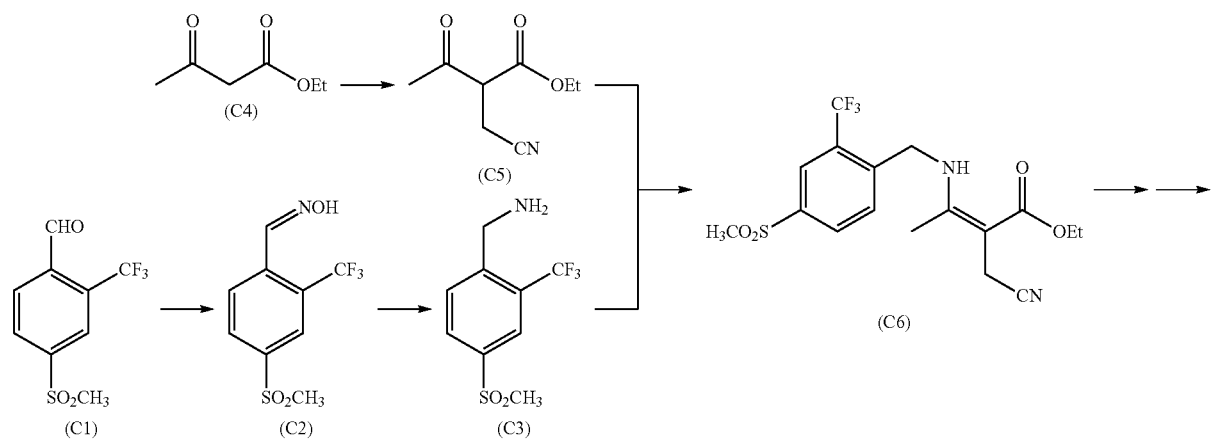

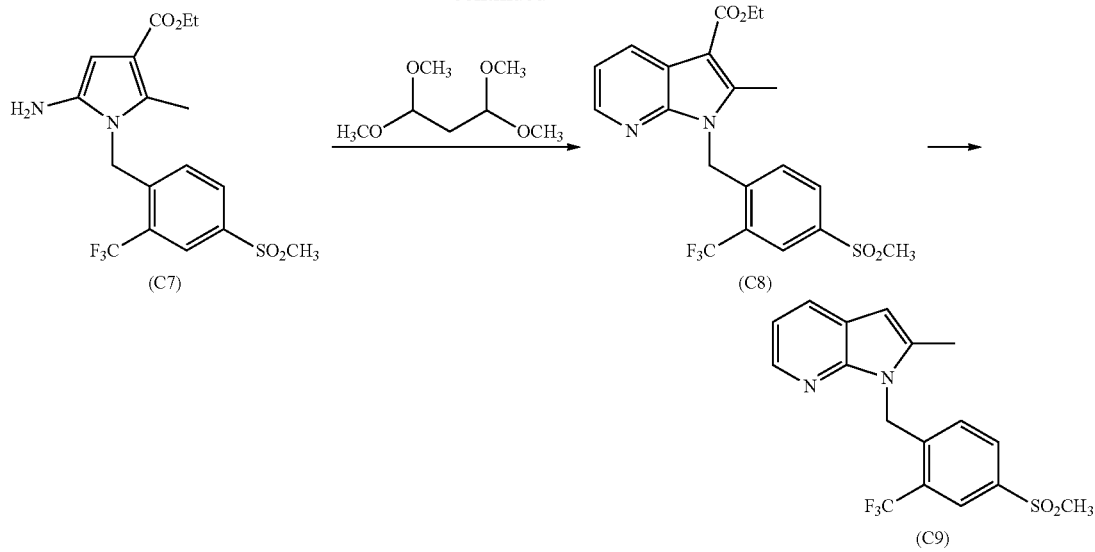
C9 is then converted into Compound A via one of several reaction schemes. These schemes follow below.
Reaction Scheme 1 for formation of Compound A from C9
Reaction Scheme 2 for formation of Compound A from C9
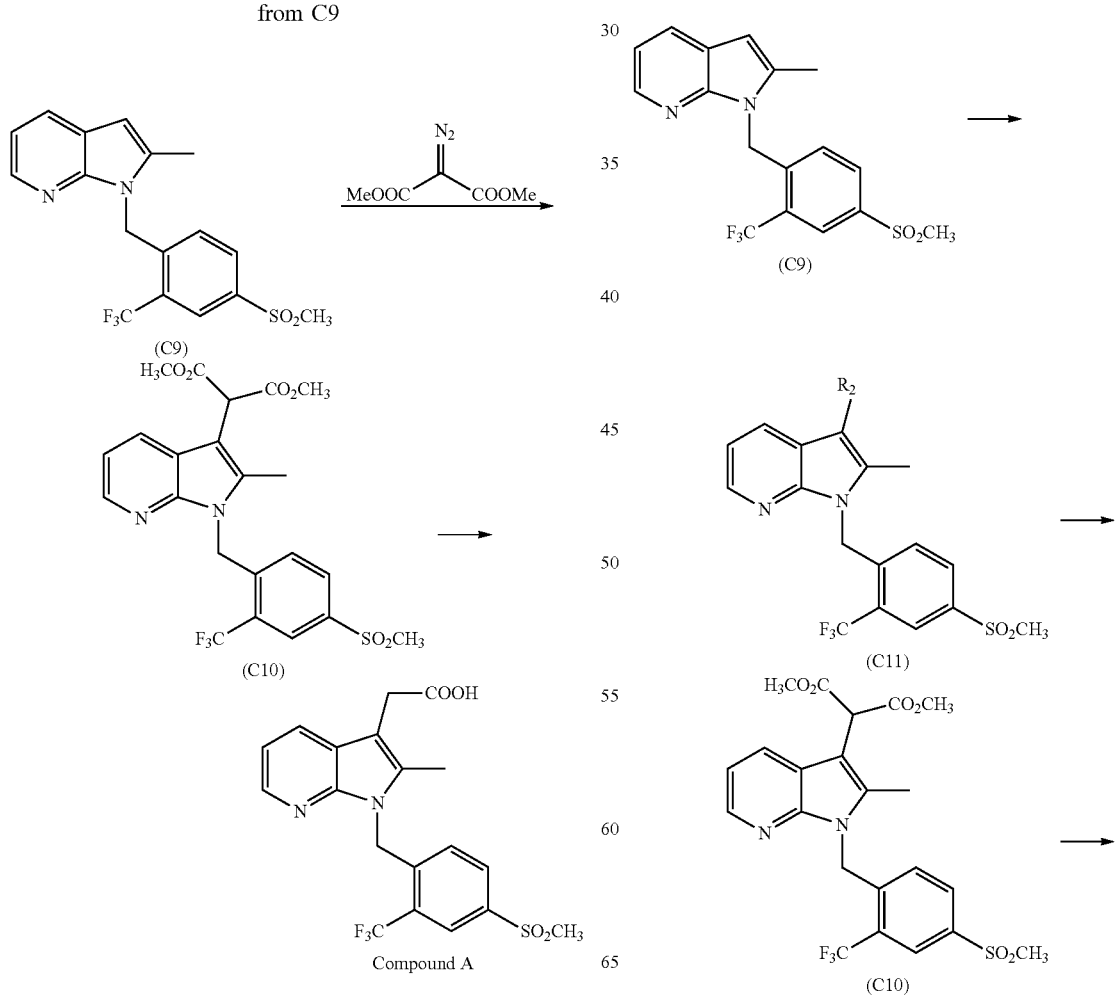

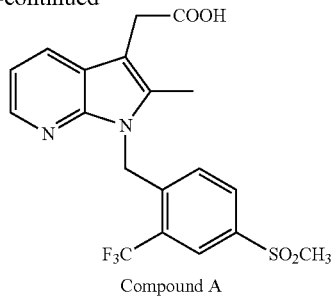

Compound A

The current scheme of the invention advantageously increases yields and selectivity of Compound A by first creating intermediate C9. Thereafter, C9 is easily converted into Compound A via one of several reaction schemes. The overall scheme for the production of Compound A is cheap, robust, fast e.g., short cycle times), and safe as the reactions can be carried out without the use of cryogenic reaction conditions.

The process scheme starts with the formation of intermediate C6 from C5 and C3, each of which are first synthesized. To form C3, C1 is converted to C2 by adding hydroxylamine hydrochloride in the presence of one or more solvents such as water, ethanol (EtOH), dimethyl sulfoxide (DMSO) or other known solvents. Furthermore, the reaction is under basic conditions by adding a strong Lewis base such as sodium hydroxide. Suitable reaction times are in the range of 0.5-48 h. The preferred range is 1.0-10 h. Suitable reaction temperatures are from 0-80° C., with 10-40° C. being preferred.

Compound C2 is then converted to C3 in the presence of ethyl acetate (EA) and a catalyst such as palladium on charcoal. Suitable reaction times are in the range of 0.5-48 h. The preferred range is 10-30 h. Suitable reaction temperatures are from 0-80° C., with 10-50° C. being preferred.

In parallel, C4 is reacted with a compound of the formula:

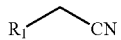

wherein R1 is a halogen selected from the group consisting of chloro, bromo or iodo in the presence of one or more solvents such as water, dichloro methane, EtONa and the like to form C5. Other alcoholate bases, compatible with the ester, such as NaOH, t-BuOK, t-BuONa KOH, and K2CO3, can be used in this step as well. In another embodiment, other reagents and solvents such as benzene, toluene, xylenes, cymene, organic and mineral acids can be used. Also as known in the art, various protic, mineral, organic or Lewis acids can be used in this step, as can various tetraalkoxypropanes. Suitable reaction times are in the range of 0.5-48 h. The preferred range is 5-15 h. Suitable reaction temperatures are from 0-80° C., with 10-40° C. being preferred.

Alternative schemes for synthesizing C3 are shown in FIG. 1. Unless specifically noted herein, the synthesis of C3 is performed under various conditions which the skilled artisan would readily appreciate. For example in one embodiment, as shown in FIG. 1, C3 is formed by converting compound 101 to 103, which is then converted to 105. Compound 105 is then converted to 107, which is converted to 109 and then 111. Compound 111 is then converted to C3.

As another example, compound 113 is converted to 115. Compound 115 is then converted to 117 in the presence of sodium benzene sulfonate. Compound 117 is then converted to 119 in the presence of Dibal-H, where it is then converted to C3 in the presence of SOCl$_2$.

In yet another example, compound 121 is converted to 123, which is then converted to compound 125 in the presence of a palladium catalyst and Zn(CN)$_2$. Compound 125 can then be converted to compound 117 (where it proceeds as detailed in the proceeding example) or converted to compound 127 in the presence of Dibal-H. Compound 127 is then converted to compound 119 in the presence of sodium benzene sulfinate.

As seen in FIG. 1, in another example, compound 129 is first converted to 131. Compound 131 is then converted to compound 133 in the presence of a copper catalyst and TMSCF$_3$. Compound 133 is converted to compound 135 in the presence of sodium benzene sulfinate, which is then converted to compound 119.

Compound C6 is then formed by reacting C3 and C5 in the presence of PPA and EtOH or other similar reagents. Suitable reaction times are in the range of 0.5-48 h. The preferred range is 5-20 h. Suitable reaction temperatures are from 0-80° C., with 10-60° C. being preferred.

Compound C6 is converted to C7 by adding EtONa in the presence of an organic solvent such as ethanol and an acid such as hydrochloric acid. In other embodiments, other organic solvents and strong acids known in the art can be utilized. Suitable reaction times are in the range of 0.5-48 h. Suitable reaction temperatures are from 0-80° C., with 10-40° C. being preferred.

C7 is then converted to C8 by reacting it with 1,1,3,3-Tetramethoxypropane in the presence of a strong acid such as hydrochloric acid and a solvent such as ethanol. In other embodiments, other strong Lewis acids and other organic solvents can be used as is known in the art. Suitable reaction times are in the range of 0.5-48 h. The preferred range is 1.0-8 h. Suitable reaction temperatures are from 0-80° C., with 10-40° C. being preferred.

C8 is then converted to C9 by reacting C8 with acetic acid (HOAc) in the presence of a strong acid such as hydrochloric acid. Suitable reaction times are in the range of 0.5-48 h. The preferred range is 1.0-10 h. Suitable reaction temperatures are from 0-150° C.), with 50-120° C. being preferred.

C9 is then converted to Compound A via one of several reaction schemes. In the first, C9 is reacted with DMDA to form C10 in the presence of a catalyst and an organic solvent. In the preferred embodiment the catalyst is cupric based, preferably Cu(acc)2. Other cupric sources such as Cu(acac)2, Cu(F6-acac)2, Cu(O2CCF3)2, Cu(acac)2 with ligands like triphenylphosphine (PPh3) or 2,2'-bipyridyl, 1,10-phenanthroline are utilized in other embodiments. In the preferred embodiment, the solvent is toluene, however other organic solvents such as acetonitrile, benzene and the like can be used. Suitable reaction times are in the range of 0.5-48 h. The preferred range is 2-20 h. Suitable reaction temperatures are from 0-150° C.), with 50-120° C. being preferred.

C10 is then converted to Compound A by reacting sodium hydroxide in the presence of an alcohol such as ethanol. In other embodiments any other organic alcohol can be utilized. Suitable reaction times are in the range of 0.5-48 h. The preferred range is 2-20 h. Suitable reaction temperatures are from 0-150° C., with 50-120° C. being preferred.

In another embodiment, compound C9 is first reacted with a halogen in the presence of a solvent such as dimethyl formate (DMF) to form C11. The halogen compound is preferably a compound selected from the group consisting of chlorine, bromine, iodine, or fluorine. In a preferred embodiment the halogen is iodine. Compound C11 is then reacted with DMM in the presence of a polar aprotic solvent, a ligand and a catalyst to form C10. Preferred catalysts are copper based such as CuI, CuBr and CUCl. Suitable solvents include acetonitrile, N-butyl-pyrrolidine (NBP), tetrahydrofuran (THF), methyl tetrahydrofuran (MeTHF), water surfactants and combinations thereof. Suitable ligands include $K_2CO_3$. Suitable reaction times are in the range of 0.5-96 h. The preferred range is 5-48 h. Suitable reaction temperatures are from 0-150° C., with 50-120° C. being preferred. Compound C10 is then converted to Compound A as described above.

EXPERIMENTAL EXAMPLES

The following experimental examples illustrate the processes of the present invention and are not intended to limit the scope of the present invention as defined in the claims below.

Example 1: Preparation of C2 (4-(methanesulfonyl)-2-(trifluoromethyl) benzaldehyde oxime)

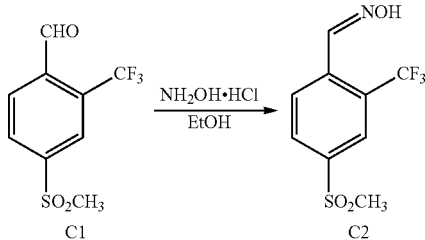

Example 1 Raw Materials

| Materials | mw | Eq. | G |
|---|---|---|---|
| C1 | 252.21 | 1 | 277 |
| 95% EtOH | — | — | 1320 |
| Hydroxylamine hydrochloride | 70.49 | 1.2 | 91.5 |
| $H_2O$ | 18 | — | 2230 |
| 10% NaOH | — | — | 630 |

Example 1 Procedure

1. Compound C1 (277 g) and 95% EtOH (1320 g) were charged into the reactor at 20~30° C. Then the mixture was stirred for 0.5 h at 20~30° C.
2. While maintaining the temperature at 20~30° C., a solution of Hydroxylamine hydrochloride (91.5 g) in water (230 g) was added into the mixture.
3. The mixture was heated to 25~35° C. for reaction. After 2 h, the mixture was sampled to be analyzed by TLC.
4. The mixture was evaporated to remove ethanol, and then water (1000 g) was charged into the reactor.
5. The mixture was cooled to 5~10° C., and 10% NaOH solution (630 g) was added dropwise at 10° C.~20° C. to adjust pH=8~9.
6. The mixture was filtered with a nutsche filter. The filter cake was rinsed with water (1000 g).
7. The filter cake was dried at 40~45° C. on vacuum to afford compound C2.

Example 1 Results

| Example NO. | Input of C1 (raw material)/g | Output C2/g | yield |
|---|---|---|---|
| 1 | 277 | 285.9 | 97.4% |

Examples 2 and 3: Preparation of C3 (4-(methanesulfonyl)-2-(trifluoromethyl)phenyl)methanamine)

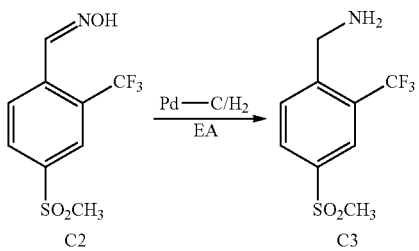

Examples 2 and 3 Starting Materials

| NO. | Materials | Mw | Eq. | g |
|---|---|---|---|---|
| 1 | Compound C2 | 267.22 | 1.0 | 133.3 |
| 2 | Pd—C | — | 0.1 | 13 |
| 3 | EA | — | — | 890 |
| 4 | 36% hydrochloric acid | 37.5 | — | 89 |
| 5 | water | — | — | 700 |
| 6 | EA | — | — | 250 |
| 7 | 10% NaOH | — | — | 1070 |
| 8 | EA | — | — | 610 |
| 9 | Brine | — | — | 600 |
| 10 | Petroleum ether | — | — | 1340 |

Examples 2 and 3 Procedure

1. Compound C2 (133.3 g) and EA (890 g) were charged into the reactor at 20~30° C. Then the mixture was stirred for 0.5 h at 20-30° C.
2. Palladium on Charcoal (Pd—C) (13 g, 10%) was added into the mixture.
3. The mixture was flushed twice with hydrogen and then heated to 45~50° C. under a hydrogen pressure of 1 atm. After 24 h, the mixture was sampled to be analyzed by TLC.
4. The mixture was filtered with a nutsche filter. The filter cake was rinsed with EA (100 g). The filtrates were combined.
5. 1.4N hydrochloric acid prepared by conc. hydrochloric acid (89 g) and water (700 g) was added into the filtrate to adjust pH=1~2 at 20~25° C. Then the mixture was stirred for 1~2 h at 20~25° C.
6. The aqueous layer was washed with EA (250 g) and then was added dropwise with 10% NaOH (1070 g) to adjust pH=10~11.

7. The mixture was extracted with EA (610 g). The organic layer was washed with brine (600 g) and evaporated to yield the crude compound C3.
8. The crude product was stirred in petroleum ether (1340 g) at 20-30° C. for 2 h.
9. The mixture was filtered with a nutsche filter. The filter cake was rinsed with PE (100 g).
10. The filter cake was dried at 40~45° C. on vacuum to afford C3.

Examples 2 and 3 Results

| Example NO. | Input C2 (raw material)/g | Output C3/g | yield |
|---|---|---|---|
| 2 | 133.6 | 82.6 | 65.2% |
| 3 | 133.6 | 82.5 | 65.3% |

Example 4: Preparation of C5
(2-Cyano-3-oxo-butyric acid ethyl ester)

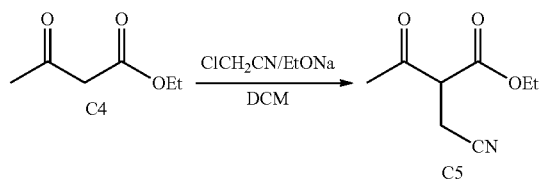

Example 4 Starting Materials

| Num | Materials | mw | Eq. | g |
|---|---|---|---|---|
| 1 | Compound C4 | 130.14 | 1.5 | 507.6 |
| 2 | Chloroacetonitrile | 75.5 | 1 | 196.5 |
| 3 | EtONa | 68.05 | 1 | 184.5 |
| 4 | NaI | 149.89 | 0.08 | 3.9 |
| 5 | DCM | — | — | 921 |
| 6 | H$_2$O | — | — | 750 |
| 7 | DCM | — | — | 520 |
| 8 | H$_2$O | — | — | 750 |

Example 4 Procedure

1. EtONa (184.5 g), NaI (3.9 g) and DCM (921 g) were charged into the reactor at 20~30° C. Then the mixture was stirred for 0.5 h at 20~30° C.
2. While maintaining the temperature at 20~35° C., C4 was added dropwise into the mixture.
3. Chloroacetonitrile was added dropwise into the mixture at 20~35° C.,
4. The mixture was heated to 25~35° C. for reaction. After 12 h, the mixture was sampled to be analyzed by GC.
5. Water (750 g) was added into the mixture at 20~25° C.
6. The mixture was stirred for 30 min at this temperature and organic layer was separated.
7. The aqueous was extracted with DCM (520 g). The combined organic layer was washed with water (750 g).
8. The organic was evaporated to yield the crude C5.
9. The crude product was distilled twice on vacuum to meet content of C5 less than 0.5%.

Example 4 Results

| Example NO. | Input C4 (raw material)/g | Output C5/g | Yield | Purity |
|---|---|---|---|---|
| 4 | 507.6 | 272.6 | 62.0% | 92.8% |

Example 5: Preparation of C6 ((Z)-3-(1-ethoxyvinyl)-4-((4-(methylsulfonyl)-2-trifluoromethyl)benzyl)amino)pent-3-enenitrile)

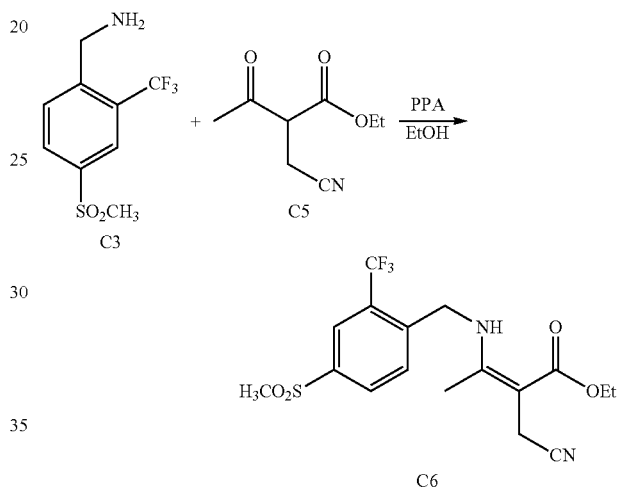

Example 5 Starting Materials

| NO. | Materials | Mw | Eq. | G |
|---|---|---|---|---|
| 1 | Compound C3 | 253.24 | 1 | 126.7 |
| 2 | PPA | — | — | 2.5 |
| 3 | EtOH | — | — | 1580 |
| 4 | Compound C5 | 169.18 | 1 | 84.5 |
| 5 | EtOH | — | — | 395 |

Example 5 Procedure

1. Compound C3 (126.7 g) and EtOH (1580 g) were charged into the reactor at 20~30° C. Then the mixture was added PPA (2.5 g) and stirred for 0.5 h at 20~30° C.
2. While maintaining the temperature at 20~30° C., C5 (84.5 g) was added dropwise into the mixture.
3. The mixture was heated to 45~50° C. for reaction. After 16 h, the mixture was sampled to be analyzed by TLC.
4. The mixture was cooled to 10~15° C.
5. The mixture was filtered with a nutsche filter. The filter cake was rinsed with EtOH (395 g).
6. The filter cake was dried at 40~45° C. on vacuum to afford compound C6.

Example 5 Results

| Example NO. | Input C3, C5 (raw material)/g | Output C6/g | yield |
|---|---|---|---|
| 5 | 126.7; 84.5 | 147.7 | 73.1% |

Examples 6 and 7: Preparation of C8 (ethyl 2-methyl-1-(4-(methylsulfonyl)-2-(trifluoromethyl) benzyl)-1H-pyrrolo[2,3-b]pyridine-3-carboxylate)

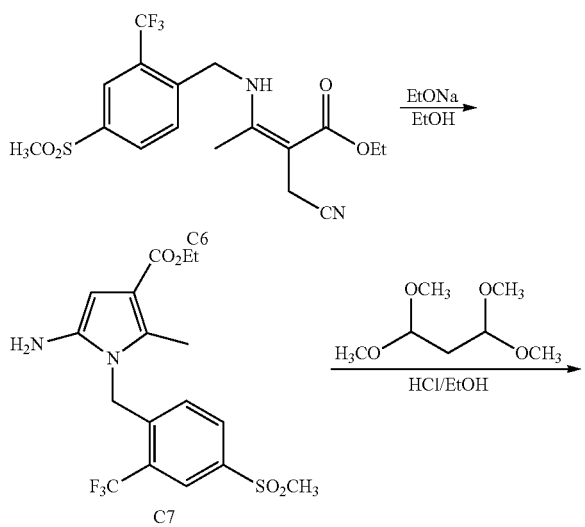

Examples 6 and 7 Starting Materials

| NO. | Materials | Mw | Eq. | g |
|---|---|---|---|---|
| 1 | Compound C6 | 404.40 | 1 | 161.7 |
| 2 | EtONa | 68.05 | 1.25 | 32.7 |
| 3 | EtOH | — | — | 1185 |
| 4 | 6.7% HCl/EtOH | — | — | 656 |
| 5 | 1,1,3,3-tetramethoxypropane | 164.20 | — | 131.2 |
| 6 | EtOH | — | — | 158 |
| 7 | EA | — | — | 1800 |
| 8 | 10% NaOH | — | — | 500 |
| 9 | Brine | — | — | 200 |
| 10 | EtOH | — | — | 553 |

Examples 6 and 7 Procedure

1. EtOH (1185 g) and EtONa (32.7 g) were charged into the reactor at 20~30° C. Then the mixture was stirred for 0.5 h at 20~30° C.
2. While maintaining the temperature at 20~30° C., compound C6 (161.7 g) was added into the mixture by portions.
3. The mixture was stirred for 2 h at this temperature. The mixture was sampled to be analyzed by TLC.
4. The mixture was cooled to 10~20° C., then HCl/EtOH (6.7%, 656 g) was charged into the reactor.
5. While maintaining the temperature at 20~30° C., 1,1,3,3-tetramethoxypropane (131.2 g) was added into the mixture.
6. The mixture was cooled to 20~25° C.
7. The mixture was filtered with a nutsche filter. The filter cake was rinsed with water (158 g).
8. EA (1800 g) and the filter cake (230 g) were added into the reactor.
9. The mixture was added dropwise 10% NaOH (500 g) to adjust pH 8~9.
10. The organic layer was separated and washed with bine (200 g).
11. The organic was evaporated to yield the crude compound C8.

Examples 6 and 7 Results

| Example NO. | Input (raw material)/g | Output/g | yield |
|---|---|---|---|
| 6 | 161.7 | 130.5 | 74.1% |
| 7 | 161.7 | 132.0 | 74.9% |

Examples 8-10: Preparation of C9 (1-(2-(trifluoromethyl)-4-(methylsulfonyl)benzyl)-2-methyl-1H-pyrrolo[2,3-b]pyridine)

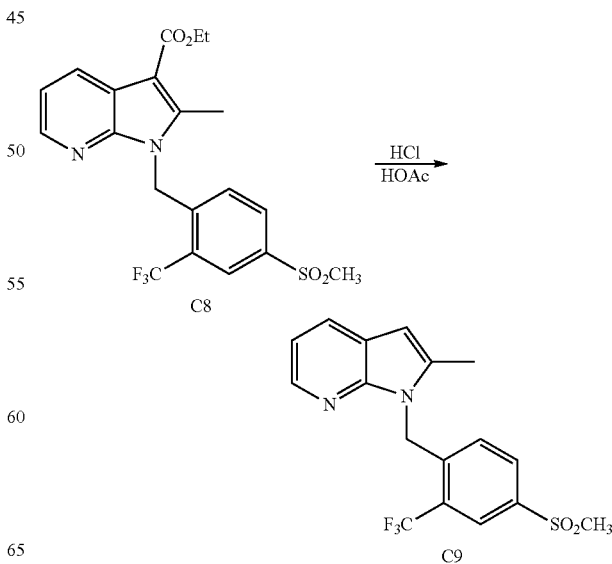

Example 8 Starting Materials

| NO. | Materials | Mw | Eq. | g |
|---|---|---|---|---|
| 1 | Compound C8 | 440.44 | 1 | 120.0 |
| 2 | HOAc | 68.05 | 1.25 | 800 |
| 3 | Conc. HCl | — | — | 958 |
| 4 | EA | — | — | 900 |
| 5 | 20% NaOH | — | — | 200 |
| 6 | brine | — | — | 200 |
| | Purification | | | |
| 8 | Crude compound C9 | 368.37 | — | 260 |
| 9 | MeOH | — | — | 1106 |
| 10 | Water | — | — | 300 |
| 11 | MeOH | — | — | 120 |

Example 8 Procedure

1. HOAc (800 g) and compound C8 (120 g) were charged into the reactor at 20~30° C. Then the mixture was stirred for 0.5 h at 20~30° C.
2. While maintaining the temperature at 20~30° C., concentrated hydrochloric acid (958 g) was added into the mixture in one portion.
3. The mixture was heated to 100~105° C. for reaction. After 4 h, the mixture was sampled to be analyzed by TLC.
4. The mixture was cooled to 60~70° C. and evaporated.
5. EA (900 g) were added into the reactor.
6. While maintaining the temperature at 20~40° C., 20% NaOH (200 g) was added into the mixture to adjust pH 8~9.
7. The organic layer was separated and washed with bine (200 g).
8. The organic was evaporated to yield the crude compound C9.

Purification:

1. MeOH (1106 g) and the crude compound C9 (260 g) were added into the reactor.
2. The mixture was heated to 65~70° C., and then Water (300 g) was added into the mixture. Then it was stirred at this temperature for 0.5 h.
3. The mixture was cooled to 5~10° C., and then filtered with a nutsche filter. The filter cake was rinsed with MeOH (120 g).
4. The filter cake was dried at 40~45° C. on vacuum to afford compound C9.

Examples 9 and 10

The starting materials for examples 9 and 10 were nearly identical except the starting amount of compound C8 was changed to 188.1 grams (example 9) and 260 grams (example 10) respectively. The other starting materials were adjusted on an equivalents basis to compensate for the differences in the starting weight of compound C8; the procedural steps were the same for examples 9 and 10 (with the adjustment of the weights on an equivalent basis).

Examples 8-10 Results

| Experiment NO. | Input C8 (raw material)/g | Output C9/g | yield | purity |
|---|---|---|---|---|
| 8 | 120 | 100 | 100% (crude) | |
| 9 | 188.1 | 160 | 101% (crude) | |
| 10 | 260 | 214 | 83% (purified) | 99.5% |

Examples 11-13: Preparation of C11 (3-iodo-2-methyl-1-(4-(methylsulfonyl)-2-(trifluoromethyl)benzyl)-1H-pyrrolo[2,3-b]pyridine)

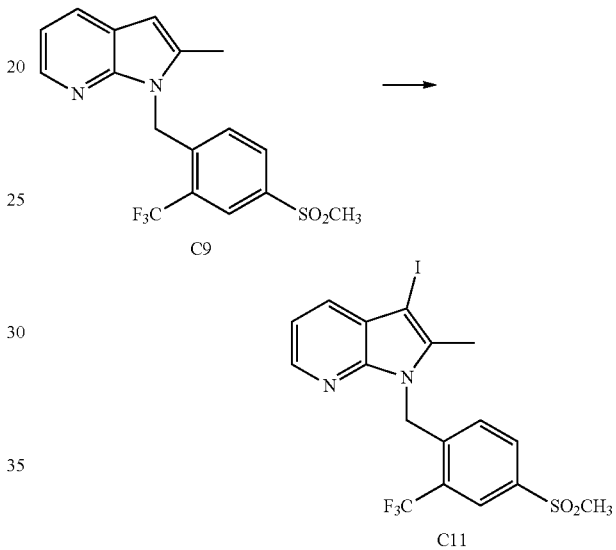

Examples 11 Starting Materials

| NO. | Materials | Mw | Eq. | g |
|---|---|---|---|---|
| 1 | Compound C9 | 368.37 | 1 | 11.05 |
| 2 | I₂ | 253.8 | 2.1 | 16.0 |
| 3 | DMF | — | — | 75 |
| 4 | 10% Na₂S₂O₄ | — | — | 200 |
| 5 | EA | — | — | 150 |
| 6 | Brine | — | — | 50 |
| 7 | EtOH | — | — | 32 |

Example 11 Procedure

1. DMF (75 g) and compound C9 (11.05 g) were charged into the reactor at 20~25° C. Then I₂ (16.0 g) was added into the mixture at 20~25° C.
2. The mixture was stirred at 20~25° C. for 24 hours.
3. While maintaining the temperature at 20~25° C., 10% Na₂S₂O₄ (200 g) was added into the mixture in one portion.
4. Then EA (150 g) was added into the mixture in one portion at 20~25° C.

5. The mixture was stirred for 30 min at this temperature and then organic layer was separated.
6. The organic layer was washed with brine (50 g).
7. The organic layer was concentrated to obtain the crude C11.
8. EtOH (32 g) and the crude compound C9 (20 g) were added into the reactor.
9. The mixture was heated to 75~80° C., and then stirred at this temperature for 1 hour.
10. The mixture was cooled to 5~10° C. and filtered. The cake was washed with EtOH (5 g).
11. The cake was dried at 40~45° C. on vacuum.

Examples 11-13

TABLE 1

Compound C11 from C9

| No. | C9 (g) | I₂ (eq.) | Solvents (mL) | Temp (° C.) | Time (h) | Yield |
|---|---|---|---|---|---|---|
| 11 | 11.05 | 2.1 | DMF (80 mL) | 20-25° C. | 24 | 91.2% (purified) |
| 12 | 1.10 | 2.1 | DCM (5 mL) DMF (0.5 mL) | 20-25° C. | 24 | 101% (crude) |
| 13 | 0.37 | 1.1 | DMF (5 mL) | 20-25° C. | 24 | Conversion: 80% |

Examples 14-22: Production of Compound 10 (methyl 2-(2-methyl-1-(4-(methylsulfonyl)-2-(trifluoromethyl)benzyl)-1H-pyrrolo[2,3-b]pyridin-3-yl)-4-(methylperoxy)but-3-ynoate) from C11

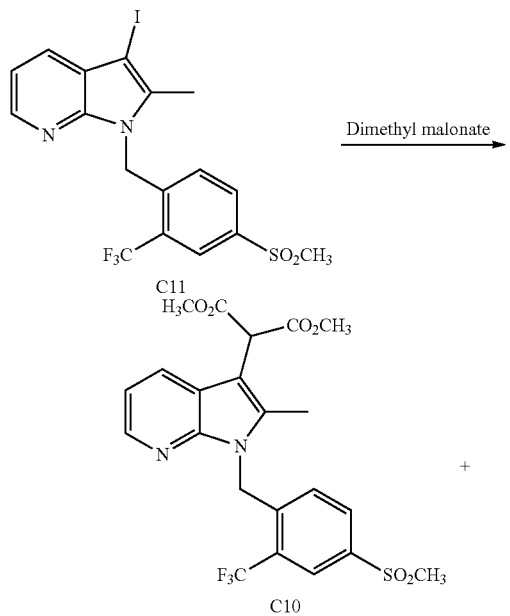

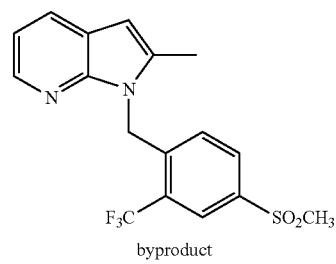

byproduct

Examples 19 Starting Materials

| NO. | Materials | Mw | Eq. | g |
|---|---|---|---|---|
| 1 | Compound C11 | 494.2 | 1 | 12.35 |
| 2 | Ligand | — | 0.4 | 1.2 |
| 3 | K₂CO₃ | 138.2 | 3.0 | 10.37 |
| 4 | DMM | 132.1 | 3.0 | 9.91 |
| 5 | CuI | 190.45 | 0.2 | 1.0 |
| 6 | DMF | — | — | 112 |
| 7 | H₂O | — | — | 100 |
| 8 | DCM | — | — | 150 |
| 9 | 5% NH₃·H₂O | — | — | 50 |
| 10 | Brine | — | — | 50 |

Example 19 Procedure

1. DMF (110 g)、K₂CO₃ (10.37 g)、ligand (1.2 g), DMM (9.91 g)、CuI (1.0 g) and compound C11 were charged into the reactor at 20~25° C. under N₂ atmosphere.
2. The mixture was heated to 68~75° C., and maintained at this temperature for 72 h. Then the mixture was analyzed by HPLC.
3. The mixture was concentrated at 68~75° C. on vacuum.
4. The residual was cooled to 20~25° C.
5. H₂O (100 g) and DCM (150 g) were added into the mixture at 20~25° C.
6. The mixture was stirred for 30 min at this temperature and then organic layer was separated.
7. The organic layer was washed with 5% NH₃.H₂O (50 g) and brine (50 g) in proper sequence.
8. The organic was concentrated to obtain crude C10.
9. The crude C10 was purified by column chromatography on silica gel (ethyl acetate/petroleum ether=1:4 as eluent) to obtain pure C10.

Examples 14-22

| No. | C11 (g) | Reagents (eq) | Solvents (mL) | Temp (° C.) | Time (h) | Result | Supplements |
|---|---|---|---|---|---|---|---|
| 14 | 0.494 | CuI (0.1) DMM (3.0) Cs$_2$CO$_3$ (3.0) ligand (0.2) | Dioxane (5 mL) | 60-100° C. | 24 | No reaction | |
| 15 | 0.247 | CuI (0.2) DMM (3.0) K$_2$CO$_3$ (3.0) ligand (0.4) | DMF (2 mL) | 95-100° C. | 20 | C11:C10:byproduct = 18%:72%:10% | |
| 16 | 0.494 | CuI (0.2) DMM (3.0) K$_2$CO$_3$ (3.0) ligand (0.4) | DMF (4 mL) | 45-50° C. | 20 | C11:C10:byproduct = 52%:45%:2% | |
| 17 | 0.247 | CuI (0.2) DMM (3.0) K$_2$CO$_3$ (3.0) ligand (0.4) | DMF (2 mL) | 78-82° C. | 20 | No reaction | |
| 18 | 2.47 | CuI (0.2) DMM (3.0) K$_2$CO$_3$ (3.0) ligand (0.4) | DMF (20 mL) | 65-70° C. | 72 | C11:C10:byproduct = 2%:85%:11% | Yield 83% |
| 19 | 12.35 | CuI (0.2) DMM (3.0) K$_2$CO$_3$ (3.0) ligand (0.4) | DMF (120 mL) | 68-78° C. | 72 | C11:C10:byproduct = 6%:66%:13% | Slow |
| 20 | 0.494 | CuI (0.1) DMM (3.0) Cs$_2$CO$_3$ (3.0) ligand (0.2) | Dioxane (5 mL) | 60-100° C. | 24 | No reaction | |
| 21 | 0.247 | CuI (0.2) DMM (3.0) K$_2$CO$_3$ (3.0) ligand (0.4) | DMF (2 mL) | 95-100° C. | 20 | C11:C10:byproduct = 18%:72%:10% | |
| 22 | 0.494 | CuI (0.2) DMM (3.0) K$_2$CO$_3$ (3.0) ligand (0.4) | DMF (4 mL) | 45-50° C. | 20 | C11:C10:byproduct = 52%:45%:2% | |

Examples 23-24: Production of Compound A from C10

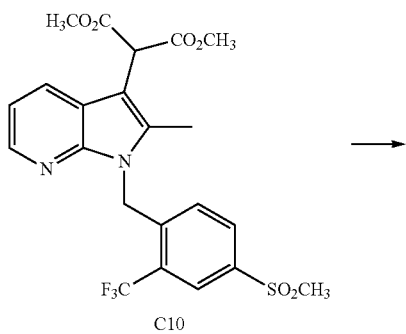

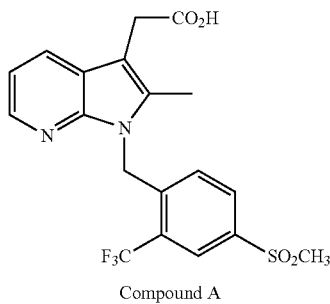

Compound A

Examples 23 Starting Materials

| NO. | Materials | Mw | Eq. | g |
|---|---|---|---|---|
| 1 | Compound C10 | 498.47 | 1 | 2.49 |
| 2 | HOAc | — | — | 10 |
| 3 | Conc. HCl | — | — | 10 |
| 4 | DCM | — | — | 30 |
| 5 | 20% NaOH | — | — | 7 |
| 6 | Conc. HCl | — | — | 2.5 |
| | Purification | | | |
| 8 | Crude compound C9 | 368.37 | — | 2.0 |
| 9 | IPA | — | — | 10 |
| 10 | Water | — | — | 4 |
| 11 | IPA | — | — | 2 |

Example 23 Procedure

1. HOAc (10 g) and compound C10 (2.49 g) were charged into the reactor at 20~30° C. Then the mixture was stirred for 0.5 hour at 20~30° C.
2. While maintaining the temperature at 20~30° C., concentrated hydrochloric acid (11.7 g) was added into the mixture in one portion.
3. The mixture was heated to 100~105° C. for reaction. After 4 h, the mixture was analyzed by TLC.
4. The mixture was cooled to 60~70° C. and concentrated.
5. DCM (30 g) was added into the reactor.

6. While maintaining the temperature at 20~40° C., 20% NaOH (7 g) was added into the mixture to adjust pH 9~10.
7. The water layer was separated.
8. While maintaining the temperature at 20~30° C., concentrated hydrochloric acid (2.5 g) was added into the mixture to adjust pH 3~4.
9. The mixture was cooled to 5~10° C. and then the mixture was stirred for 0.5 hour at 5~10° C.
10. The mixture was filtered and cake was washed with cool EtOH (2 g).
11. The filter cake was dried at 50~55° C. on vacuum.

Purification:
1. IPA (10 g) and the crude compound C9 (2.0 g) were added into the reactor.
2. The mixture was heated to 75~80° C., then water (4.0 g) was added into the mixture. Then it was stirred at this temperature for 0.5 hour.
3. The mixture was cooled to 5~10° C., and filtered. The filter cake was washed with cool IPA (2 g).
4. The filter cake was dried at 50~55° C. on vacuum to afford compound A.

Examples 23-24

| No. | C10 (g) | Reagents (eq) | Solvents (mL) | Temp. (° C.) | Time (h) | Result | Supplements |
|---|---|---|---|---|---|---|---|
| 23 | 2.49 | / | HCl (10 mL) HOAc (10 Ml) | 95-100° C. | 4 | Pure | Yield: 85% recrystal.Purity: 99.7% |
| 24 | 2.49 | KOH (2.0) | 90% EtOH (20 mL) | 78-80° C. | 16 | 95% | 90% |

Examples 25-37: Alternative Production of Compound A from C9

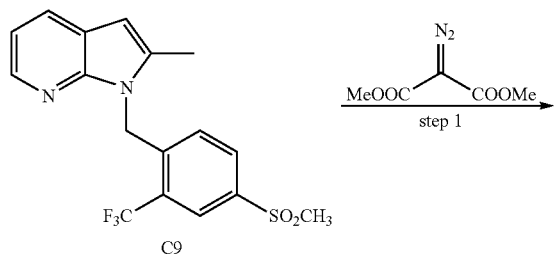

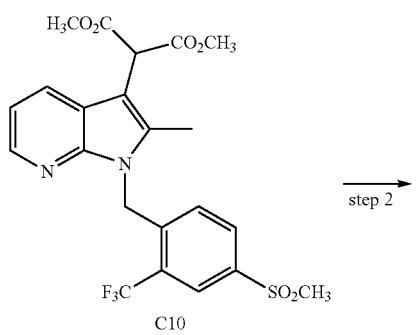

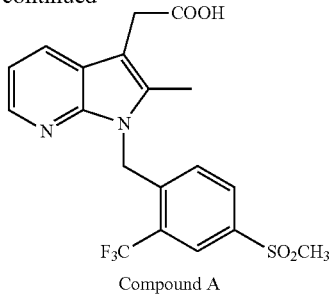

Compound A

Examples 31 Starting Materials

| NO. | Materials | Mw | Eq. | g |
|---|---|---|---|---|
| 1 | Compound C9 | 368.37 | 1 | 22.08 |
| 2 | Cu(acac)₂ | 261.76 | 0.1 | 0.18 |
| 3 | Toluene | — | — | 200 |

-continued

| NO. | Materials | Mw | Eq. | g |
|---|---|---|---|---|
| 4 | DMDA | 158.11 | 2.2 | 20.8 |
| 5 | EA | — | — | 300 |
| 6 | 5% NH₃•H₂O | — | — | 100 |
| 7 | Brine | — | — | 100 |
| 8 | EtOH | — | — | 32 |
| 9 | EtOH | — | — | 8 |

Example 31 Procedure

1. Toluene (200 g) Cu(acac)₂ and compound C9 (22.08 g) were charged into the reactor at 20~30° C. under N₂ atmosphere.
2. The mixture was heated to 90~100° C. Then DMDA (20.8 g) was dropwised into the mixture in 2.0 h under 90~100° C.
3. The mixture was stirred at 90~100° C. for reaction. After 20 h, the mixture was analyzed by TLC.
4. The mixture was cooled to 50~60° C. and concentrated on vacuum.
5. The mixture was cooled to 20~30° C. and EA (300 g) and 5% NH₃H₂O (100 g) was charged into the mixture.
6. The mixture was stirred for 30 min at this temperature and organic layer was separated.
7. The organic layer was washed with brine (100 g).
8. The organic was evaporated on vacuum to yield the crude C10.
9. EtOH (32 g) and the crude compound C10 were added into the reactor.

10. The mixture was heated to 75~80° C., and then stirred at this temperature for 1.0 h.
11. The mixture was cooled to 5~10° C. and stirred at 5~10° C. for 0.5 hour, then filtered. The filter cake was washed with cool EtOH (8 g).
12. The filter cake was dried at 60~65° C. on vacuum to the pure compound C10

Examples 25-37

| No. | C9 (g) | Reagents (eq.) | Solvents (mL) | Temp (° C.) | Time (h) | Result | Supplements |
|---|---|---|---|---|---|---|---|
| 25 | 0.37 | DMDA (2) Cu(acac)$_2$ (0.1) | Toluene | 100 | 6 | complex | |
| 26 | 3.68 | DMDA (2) Cu(acac)$_2$ (0.1) | Toluene (10 mL) | 100 | 6 | complex | Used for next step |
| 27 | 11.04 | DMDA (2.5) Cu(acac)$_2$ (0.05) | Toluene (120 mL) | 90-100 | 6 | Yield: 59% | crystallization |
| 28 | 0.368 | DMDA (2.5) CuI (0.05) | Toluene (5 mL) | 90-95 | 16 | No Reaction | |
| 29 | 0.368 | DMDA (2.5) Cu(OAc)•H$_2$O (0.05) | Toluene (5 mL) | 100 | 16 | complex | |
| 30 | 0.368 | DMDA (1.50 Cu(acac)$_2$ (0.05) | Toluene (5 mL) | 90-100 | 16 | 80% conversion | |
| 31 | 22.08 | DMDA (2.5) Cu(acac)$_2$ (0.01) | Toluene (250 mL) | 90-100 | 6 | Yield: 60% | crystallization |
| 32 | 0.368 | DMDA (2.50 Cu(CF$_3$SO$_3$)$_2$ (0.01) | DCM (5 mL) | 20-25 | 6 | No Reaction | |
| 33 | 1.105 | DMDA (2.5) Cu(acac)$_2$ (0.01) | Dimethylbenzene (250 mL) | 130-135 | 6 | complex | |
| 34 | 0.368 | DMDA (2.5) Cu(acac)$_2$ (0.01) | Dioxane (5 mL) | 90-95 | 16 | complex | |
| 35 | 0.368 | DMDA (2.5) Cu(acac)$_2$ (90.01) | Chlorobenzene (5 mL) | 90-95 | 16 | complex | |
| 36 | 3.68 | DMDA (2.5) Cu(acac)$_2$ (0.01) | DMM (30 mL) | 82-85 | 16 | Yield: 60% | crystallization |
| 37 | 11.05 | DMDA (2.5) (2,2,6,6-Tetramethyl-3,5-heptanedionato)copper (II) (0.01) | DMM (75 mL) | 94-97 | 16 | Yield: 62% | crystallization |

What is claimed is:

1. A process for preparing a compound of the formula comprising:

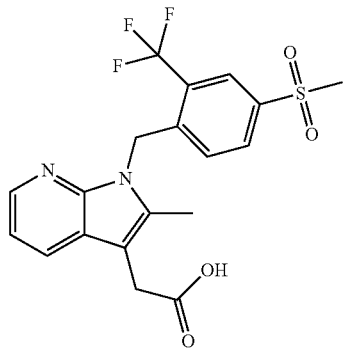

(Compound A)

[1-(4-Methanesulfonyl-2-trifluoromethyl-benzyl)-2-methyl-1H-pyrrolo[2,3-b]pyridin-3-yl]-acetic acid (a) reacting a compound of the following formula:

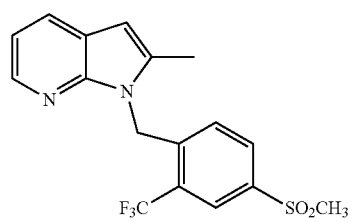

(C9)

with a compound of the following formula

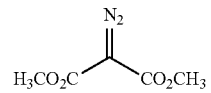

in the presence of a catalyst and an organic solvent to form the following compound:

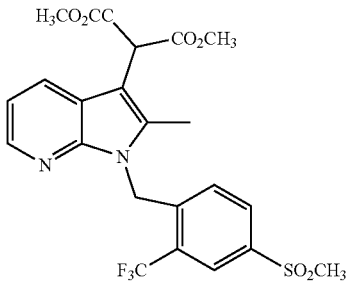
(C10)

methyl 2-(2-methyl-1-(4-(methylsulfonyl)-2-(trifluoromethyl)benzyl)-1H-pyrrolo[2,3-b]pyridin-3-yl)-4-(methylperoxy)but-3-ynoate and;

converting Compound C10 to Compound A by reacting it with a strong base or a strong acid.

2. The process according to claim 1, wherein the catalyst comprises copper.

3. The process according to claim 1, wherein the catalyst is selected from the group consisting of Cu(acc), Cu(acac)2, Cu(F6-acac)2, Cu(O2CCF3)2, and combinations thereof.

4. A process for preparing a compound of the formula

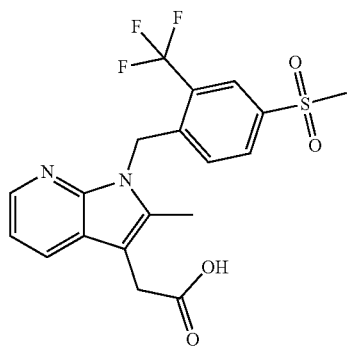
(Compound A)

[1-(4-Methanesulfonyl-2-trifluoromethyl-benzyl)-2-methyl-1H-pyrrolo[2,3-b]pyridin-3-yl]-acetic acid comprising:

(a) reacting a compound of the following formula:

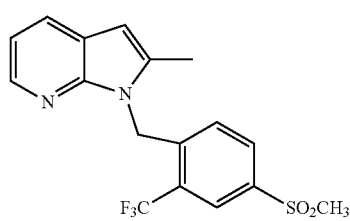
(C9)

with a halogen to form the following compound:

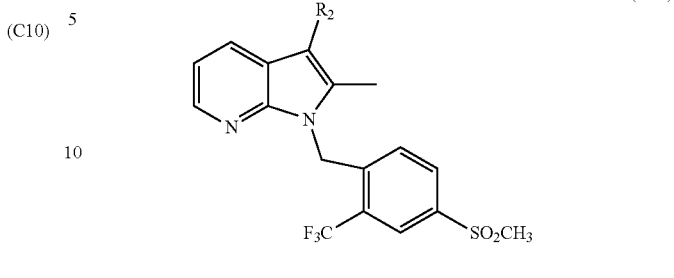
(C11)

wherein $R_2$ is a halogenated compound selected from the group consisting of chloro, bromo, iodo, or fluoro, (b) Reacting C11 with dimethyl maleate to form the following compound:

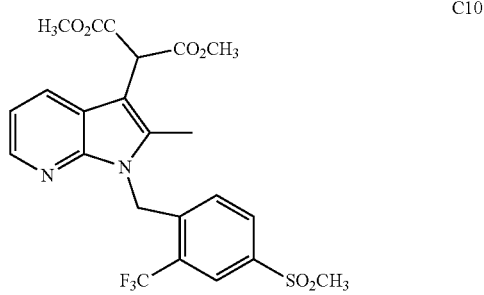
C10 and;

(c) converting Compound C10 to Compound A by reacting it with a strong base or strong acid.

5. The process of claim 4, wherein the halogen is iodine.

6. The process of claim 4, wherein the step of converting C11 to C10 further comprises reacting C11 with dimethyl maleate in the presence of a polar aprotic solvent and a ligand.

7. The process of claim 6 wherein the solvent is at least one solvent selected from the group consisting of N-butylpyrrolidine (NBP), tetrahydrofuran (THF), methyl tetrahydrofuran (MeTHF), water surfactants and combinations thereof.

8. The process of claim 4, wherein the process of converting C11 to C10 further comprises utilizing a catalyst.

9. The process of claim 8, wherein the catalyst comprises copper.

10. The process of claim 8, wherein the catalyst is at least one copper catalyst selected from the group consisting of CuI, CuBr and CuCl.

11. The process of claim 1, wherein compound C9 is produced by a process comprising:

(a) converting a compound of the formula:

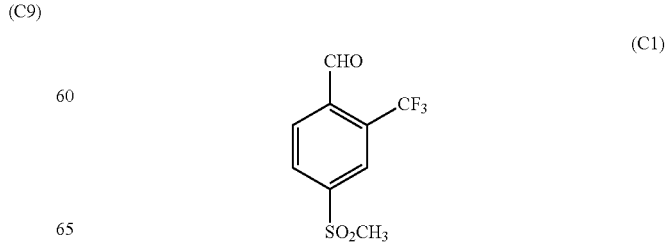
(C1)

4-(methylsulfonyl)-2-(trifluoromethyl)benzaldehyde to a compound of the following formula:

(C2)

4-(methylsulfonyl)-2-(trifluoromethyl)benzaldehyde oxime (b) converting compound C2 to a compound of the following formula:

(C3)

(4-(methylsulfonyl)-2-(trifluoromethyl)phenyl)methanamine (c) Reacting C3 with a compound of the following formula:

(C5)

ethyl 2-(cyanomethyl)-3-oxobutanoate in the presence of an organic solvent and poly-phosphoric acid (PPA) to form the following compound:

(C6)

Wherein compound C5 is formed by reacting a compound of the formula:

(C4)

ethyl 3-oxobutanoate
with a compound of the formula:

$R_1$—CH$_2$—CN wherein R1 is a halogen selected from the group consisting of chloro, bromo or iodo in the presence of one or more solvents;

(d) converting C6 to a compound of the following formula:

(C7)

ethyl 5-amino-2-methyl-1-(4-(methylsulfonyl)-2-(trifluoromethyl)benzyl)-1H-pyrrole-3-carboxylate (d) Converting C7 to a compound of the following formula:

(C8)

ethyl 2-methyl-1-(4-(methylsulfonyl)-2-(trifluoromethyl)benzyl)-1H-pyrrolo[2,3-b]pyridine-3-carboxylate
by reacting it with 1,1,3,3-Tetramethoxypropane in the presence of a strong acid and a solvent; and (e) Converting C8 to C9 by reacting C8 with an acid.

12. The process of claim 11, wherein step (a) comprises adding hydroxylamine hydrochloride in the presence of one or more solvents.

13. The process of claim 12, wherein the solvent in step (a) is at least one selected from the group consisting of water, ethanol (EtOH), and dimethyl sulfoxide (DMSO).

14. The process of claim 11, wherein step (a) occurs under basic conditions by adding a strong Lewis base.

15. The process of claim 11, wherein the conversion of step (b) occurs in the presence of ethyl acetate (EA) and a catalyst.

16. The process of claim 15, wherein the catalyst is palladium on charcoal.

17. The process of claim 11, wherein the conversion of step (d) comprises adding EtONa in the presence of an organic solvent and an acid.

18. The process of claim 11, wherein the conversion of step (e) comprises adding acetic acid.

* * * * *